(12) United States Patent
Ruokokoski et al.

(10) Patent No.: US 11,964,169 B2
(45) Date of Patent: Apr. 23, 2024

(54) APPARATUS AND METHOD FOR FORMING PRESCRIBED RADIATION THERAPY TREATMENT INSTRUCTIONS

(71) Applicant: Varian Medical Systems International AG, Steinhausen (CH)

(72) Inventors: Emmi Ruokokoski, Helsinki (FI); Ville Pietilä, Helsinki (FI); Lauri Halko, Helsinki (FI); Jarkko Y. Peltola, Tuusula (FI); Christopher Boylan, Helsinki (FI)

(73) Assignee: Varian Medical Systems International AG, Steinhausen (CH)

( * ) Notice: Subject to any disclaimer, the term of this patent is extended or adjusted under 35 U.S.C. 154(b) by 375 days.

(21) Appl. No.: 15/941,293

(22) Filed: Mar. 30, 2018

(65) Prior Publication Data

US 2019/0299025 A1    Oct. 3, 2019

(51) Int. Cl.
*A61N 5/10* (2006.01)
*G16H 10/60* (2018.01)
*G16H 20/40* (2018.01)

(52) U.S. Cl.
CPC ......... *A61N 5/1031* (2013.01); *A61N 5/1038* (2013.01); *G16H 10/60* (2018.01); *G16H 20/40* (2018.01); *A61N 2005/1074* (2013.01)

(58) Field of Classification Search
CPC .............. A61N 5/103; A61N 5/1038; A61N 2005/1074; G16H 20/40; G16H 10/60
See application file for complete search history.

(56) References Cited

U.S. PATENT DOCUMENTS

| 8,986,186 B2 * | 3/2015 | Zhang | A61N 5/103 600/1 |
| 2005/0111621 A1 * | 5/2005 | Riker | A61N 5/1031 378/65 |
| 2010/0104068 A1 * | 4/2010 | Kilby | A61N 5/1031 378/65 |
| 2010/0183121 A1 | 7/2010 | Riker | |

(Continued)

FOREIGN PATENT DOCUMENTS

| CN | 102264435 A | 11/2011 |
| CN | 102812465 A | 12/2012 |

(Continued)

OTHER PUBLICATIONS

Extended European Search Report from European Patent Application No. 19165576.0 dated Aug. 5, 2019; 6 pages.

(Continued)

*Primary Examiner* — David P Porta
*Assistant Examiner* — Casey Bryant
(74) *Attorney, Agent, or Firm* — Fitch, Even, Tabin & Flannery LLP

(57) ABSTRACT

A prescribing user can designate and prioritize clinical goals that can, in turn, serve as the basis for optimization objectives to guide the development of a radiation treatment plan. The prescribing user can then alter that prioritization of one or more clinical goals and view information regarding changes to fluence-based dose distributions that occur in response to those changes to relative prioritization amongst the clinical goals to thereby understand dosing tradeoffs that correspond to prioritization amongst the clinical goals.

19 Claims, 5 Drawing Sheets

FIG. 4

(56) References Cited

U.S. PATENT DOCUMENTS

| | | | |
|---|---|---|---|
| 2013/0326405 A1* | 12/2013 | Nord | A61N 5/103 715/810 |
| 2017/0091387 A1 | 3/2017 | Kuusela | |
| 2017/0173365 A1 | 6/2017 | Bzdusek | |
| 2018/0099151 A1* | 4/2018 | Sullivan | A61N 5/1039 |
| 2018/0169437 A1* | 6/2018 | Carpenter | A61N 5/1039 |
| 2019/0070435 A1* | 3/2019 | Joe Anto | A61N 5/1031 |
| 2019/0083813 A1 | 3/2019 | Ruokokoski | |

FOREIGN PATENT DOCUMENTS

| | | | | |
|---|---|---|---|---|
| CN | 105793854 A | 7/2016 | | |
| CN | 110114117 A | 8/2019 | | |
| EP | 3228356 A1 | 10/2017 | | |
| WO | WO-2017178257 A1 * | 10/2017 | | A61N 5/103 |
| WO | 2018122251 A1 | 7/2018 | | |

OTHER PUBLICATIONS

Chinese First Office Action from related Chinese Patent Application No. 201910249776.X dated Aug. 17, 2022, Including English translation; 18 pages.

Chao, S. "American Society for Radiation Oncology 2016 Annual Meeting: Central Nervous System Abstracts." in: Am Soc Clin Oncol Educ Book. 2017;37:171-174. doi: 10.1200/EDBK_175570_ PMID: 28561707.

* cited by examiner

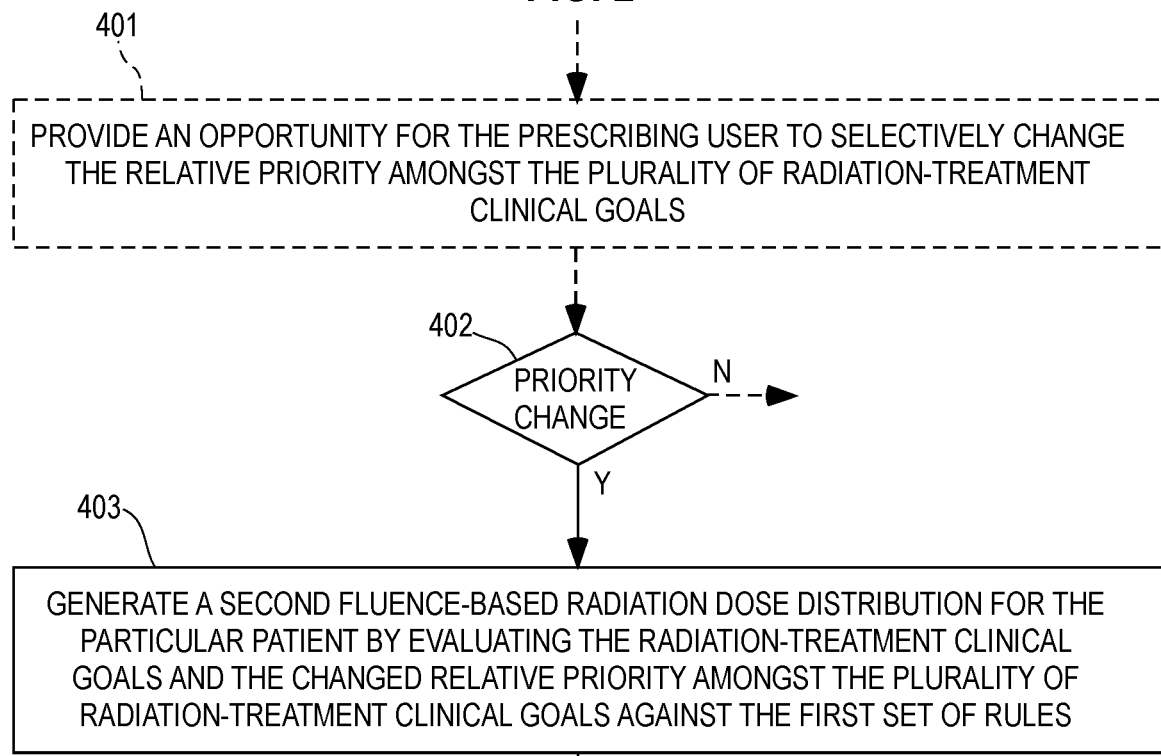
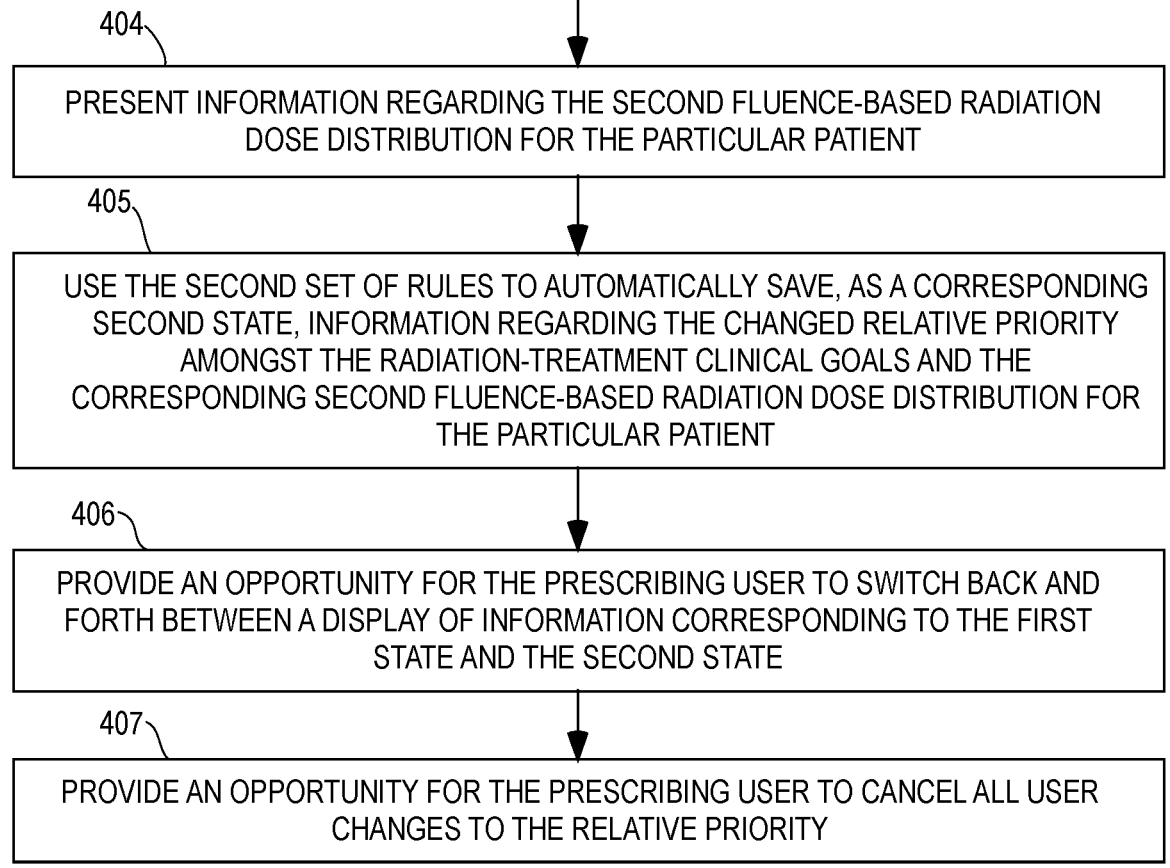
FIG. 4

APPARATUS AND METHOD FOR FORMING PRESCRIBED RADIATION THERAPY TREATMENT INSTRUCTIONS

TECHNICAL FIELD

These teachings relate generally to the formation and application of radiation therapy treatment plans and more particularly to the prioritization of clinical goals upon which treatment plans are formed and optimized.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient while using a particular radiation treatment platform. For example, many treatment plans provide for exposing the target volume to possibly varying dosages of radiation from a number of different directions. Arc therapy, for example, comprises one such approach.

Such treatment plans are often optimized prior to use. It will be understood that the expression "optimize," "optimized," and "optimizing" as used herein should not be confused with the idea of identifying an objectively "optimum" plan that is superior to all other possible plans. Instead, such optimization comprises iteratively assessing alternatives to a given plan to typically identify a series of successively-better plans. This can comprise, for example, trying and evaluating iterative alterations to each (or many) of the aforementioned operating parameters. As a specific example in these regards, when optimizing a radiation treatment plan with respect to a multi-leaf collimator, the optimization process typically seeks an optimal position for each pair of leaves independent of all other leaf pairs (for each field of exposure) by iteratively testing a variety of such positions.

Many treatment plan optimization techniques, such as so-called inverse planning, require the setting of optimization objectives. Optimization objectives provide a measure by which the process can test or assure that a particular specified dose is being uniformly administered through the patient's target volume while avoiding undue dosing of other patient tissues (or, in other cases, that a series of dose histograms that specify acceptable dosing ranges for a variety of locations both in and external to the target volume are met).

Accordingly, optimization objectives will be understood to be objectives that are very much specifically designed to reflect and accommodate the technical details and specifications of a particular radiation treatment platform, specific details regarding the patient's presentation, and/or other physical details pertaining to a particular application setting. Such details are generally viewed as being outside the expertise and knowledge base of the person who prescribes the radiation treatment in the first place (i.e., for example, a licensed oncologist). As a result, the person prescribing the radiation treatment ordinarily does not also create the optimization objectives.

Instead, the prescribing person specifies radiation-treatment clinical goals. These clinical goals are generally expressed in terms that are agnostic with respect to a specific application setting (including the radiation treatment platform itself). For example, the prescribing user may prescribe a particular minimum or maximum radiation dosage for various treatment volumes (i.e., the tissue being targeted, such as a tumor) and so-called organs at risk for which radiation exposure is to be minimized.

In a typical case there may be a plurality of radiation-treatment clinical goals, in which case the prescribing user also may be permitted to establish a relative priority amongst those goals. Unfortunately, while a prescribing user may have a general sense about how prioritization of such goals will impact formation of the corresponding radiation treatment plan, that understanding will often be relatively general in nature. As a result, the prescribing user will typically not have a good sense of what dosing trade-offs may correspond to particular prioritization choices amongst various radiation-treatment clinical goals.

BRIEF DESCRIPTION OF THE DRAWINGS

The above needs are at least partially met through provision of the apparatus and method for forming prescribed radiation therapy treatment instructions described in the following detailed description, particularly when studied in conjunction with the drawings, wherein:

FIG. 4 comprises a flow diagram as configured in accordance with various embodiments of these teachings.

Figure 1:
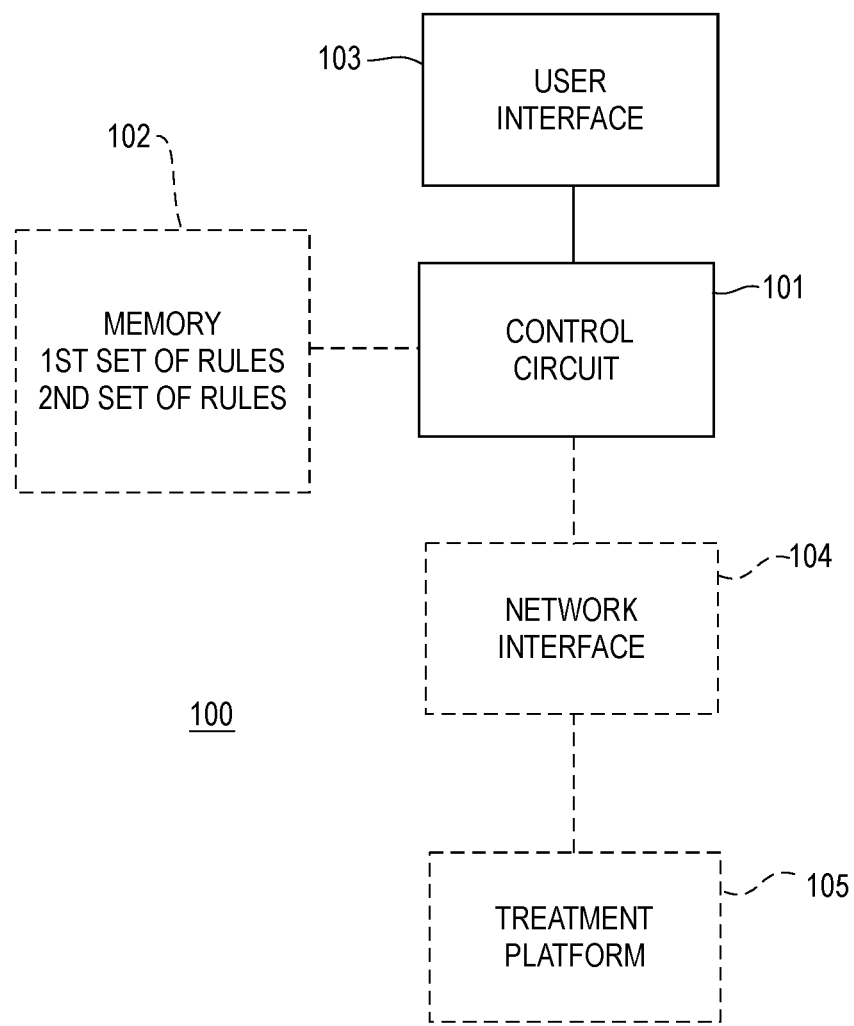
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments serve to form prescribed treatment instructions for a particular patient's radiation therapy. The prescribed treatment instructions are configured for use to determine corresponding radiation treatment plan optimization objectives that are utilized in the creation of an optimized radiation treatment plan using automatically-iterated radiation treatment plan optimization. These teachings provide for using a user interface and a control circuit operably coupled to that user interface.

These teachings provide for presenting on the user interface a plurality of radiation-treatment clinical goals having an initial-state relative priority amongst themselves as established by a prescribing user. By one approach the aforementioned relative priority is established and represented by a relative position of the goals with respect to one another. These teachings will accommodate essentially any number of radiation-treatment clinical goals.

These teachings then provide for determining a first fluence-based radiation dose distribution for the particular patient as a function of the plurality of radiation-treatment clinical goals and the relative priority amongst the plurality of radiation-treatment clinical goals and presenting information regarding the first fluence-based radiation dose distribution for the particular patient. Information regarding the relative priority amongst the plurality of radiation-treatment clinical goals and the corresponding first fluence-based radiation dose distribution for the particular patient can then be automatically saved as a corresponding first state. By one approach, the saved information comprises fluence information but does not comprise corresponding calculated dose distribution results.

Upon the prescribing user then changing the relative priority amongst the plurality of radiation-treatment clinical goals, these teachings provide for dynamically determining a second fluence-based radiation dose distribution for the particular patient as a function of the plurality of radiation-treatment clinical goals and the changed relative priority amongst the plurality of radiation-treatment clinical goals. By one approach, the prescribing user changes the relative priority by selecting and moving, on the user interface, a given one of the radiation-treatment clinical goals in order to change the relative position of that goal with respect to one or more of the other radiation-treatment clinical goals.

Information regarding that second fluence-based radiation dose distribution for the particular patient is then presented. Information regarding the changed relative priority amongst the plurality of radiation-treatment clinical goals and the corresponding second fluence-based radiation dose distribution for the particular patient is then automatically saved as a corresponding second state.

By one approach, the foregoing activities are based, at least in part, upon use of a first set of rules that define a fluence-based radiation dose distribution as a function of the plurality of radiation-treatment clinical goals and the relative priority amongst the plurality of radiation-treatment clinical goals. In addition, the foregoing activities can be based, at least in part, upon use of a second set of rules that specify automatically saving, as corresponding states, information regarding relative priorities amongst the plurality of radiation-treatment clinical goals and corresponding fluence-based radiation dose distributions as a function of detecting changes to the relative priorities amongst the plurality of radiation-treatment clinical goals.

Accordingly, as one illustrative example, these teachings can provide for formulating patient treatment prescription instructions for radiation therapy, which prescribed treatment instructions are configured for use to determine corresponding radiation treatment plan optimization objectives for creation of an optimized radiation treatment plan, by providing a user interface and presenting on the user interface a plurality of radiation-treatment clinical goals having an initial-state relative priority amongst themselves. This approach then determines a first fluence-based radiation dose distribution for a patient as a function of the plurality of radiation-treatment clinical goals and the initial-state relative priority amongst the plurality of radiation-treatment clinical goals and presents information regarding the first fluence-based radiation dose distribution for the patient and. Per this approach one then automatically saves, as a corresponding first state, information regarding the relative priority amongst the plurality of radiation-treatment clinical goals and the corresponding first fluence-based radiation dose distribution for the patient.

In response to changing, via the user interface, the relative priority amongst the plurality of radiation-treatment clinical goals, these teachings can provide for dynamically determining a second fluence-based radiation dose distribution for the patient as a function of the plurality of radiation-treatment clinical goals and the changed relative priority amongst the plurality of radiation-treatment clinical goals and presenting information regarding the second fluence-based radiation dose distribution for the patient, followed by automatically saving, as a corresponding second state, information regarding the changed relative priority amongst the plurality of radiation-treatment clinical goals and the corresponding second fluence-based radiation dose distribution for the particular patient.

In this example one then displays, on the user interface, visual information regarding changes to fluence-based dose distribution information that occur in response to changes to relative prioritization amongst the plurality of radiation-treatment clinical goals to thereby illustrate dosing tradeoffs that correspond to prioritization amongst the radiation-treatment clinical goals.

By one approach presenting on the user interface the plurality of radiation-treatment clinical goals having a relative priority amongst themselves comprises presenting the radiation-treatment clinical goals in an order of presentation, wherein a relative position of a particular one of the radiation-treatment clinical goals establishes the relative priority for that particular one of the radiation-treatment clinical goals.

By one approach a user selectively changes the relative priority amongst the plurality of radiation-treatment clinical goals by selecting and moving (for example, by clicking-and-dragging), on the user interface, the relative position of at least one of the radiation-treatment clinical goals.

These teachings are highly flexible in practice and will accommodate various modifications and supplemental functionality. For example, the prescribing user can be provided an opportunity, via the user interface, to switch back and forth between a display of information corresponding to the first state and the second state. As another example, the prescribing user can be provided with an opportunity, via the user interface, to cancel all user changes to the foregoing relative priority and thereby revert to presenting the plurality of radiation-treatment clinical goals using the initial-state relative priority amongst themselves along with the information regarding the first fluence-based radiation dose distribution for the particular patient.

So configured, the prescribing user receives visual information regarding changes to fluence-based dose distribution information that occur in response to changes by the prescribing user to relative prioritization amongst the plurality of radiation-treatment clinical goals to thereby illustrate dosing trade-offs that correspond to prioritization amongst the radiation-treatment clinical goals.

These and other benefits may become clearer upon making a thorough review and study of the following detailed description. Referring now to the drawings, and in particular to FIG. 1, an illustrative apparatus 100 that is compatible with many of these teachings will now be presented.

In this illustrative example the apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

By one optional approach the control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to a first and second set of rules and other data as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

The control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user. For the sake of this description it will be presumed that the user interface 103 at least includes a touch-screen display.

If desired, the control circuit 101 can operably couple to a network interface 104. So configured the control circuit 101 can communicate with other elements (both within the apparatus 100 and external thereto) via the network interface 104. Network interfaces, including both wireless and non-wireless platforms, are well understood in the art and require no particular elaboration here.

The control circuit 101 can also optionally operably couple (directly or indirectly) to a radiation treatment platform 105 configured to deliver therapeutic radiation to a corresponding patient in accordance with an optimized radiation treatment plan as described herein.

In a typical application setting the radiation treatment platform 105 will include an x-ray source (for example, a radio-frequency (RF) linear particle accelerator-based (linac-based) x-ray source, such as the Varian Linatron M9). A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons.

A typical radiation treatment platform 105 may also include one or more support surfaces (such as a couch) to support the patient during the treatment session, a gantry or other mechanism to permit selective movement of the x-ray source (along, for example, an arcuate pathway), a computer to optimize a radiation treatment plan, and one or more components (such as jaws, multi-leaf collimators (including both mono-layer multi-leaf collimators and multi-layer multi-leaf collimators), and so forth) to provide selective beam shaping and/or beam modulation as desired.

As the foregoing elements and systems are well understood in the art, further elaboration in these regards is not provided here except where otherwise relevant to the description.

Figure 2:
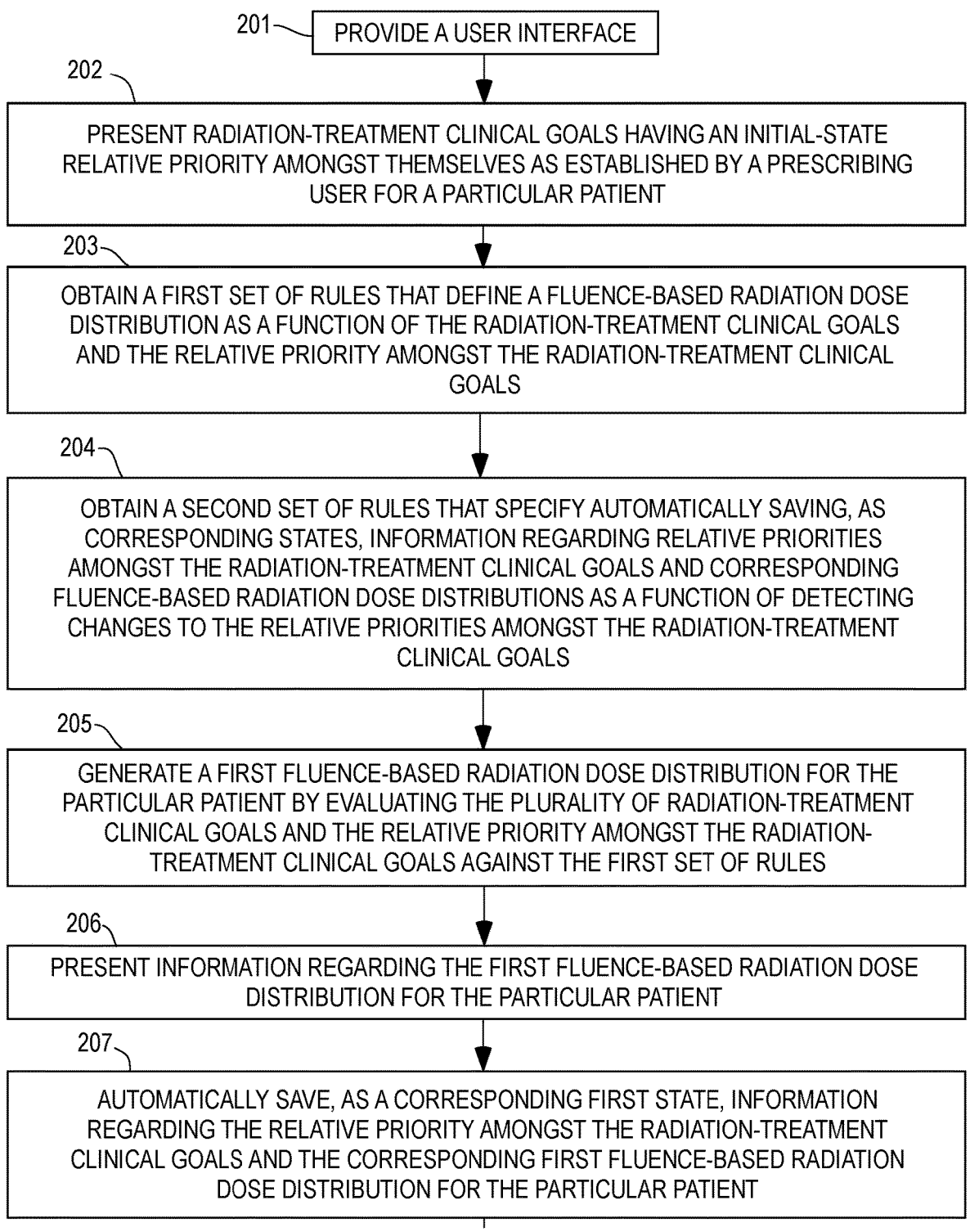
FIG. 2 comprises a flow diagram as configured in accordance with various embodiments of these teachings.

Referring now to FIG. 2 (and with continued reference to FIG. 1), a process 200 to form prescribed treatment instructions for a particular patient's radiation therapy will be presented. It will be presumed for the purposes of this description that the above-described control circuit 101 carries out the various steps, actions, and functions described in this process 200.

It will be understood that the prescribed treatment instructions are configured for use to determine corresponding radiation treatment plan optimization objectives which themselves are then used to create an optimized radiation treatment plan using automatically-iterated radiation treatment plan optimization techniques. To be clear, and as will be well understood by persons skilled in the art, the prescribed treatment instructions are not the same as optimization objectives. Instead, the prescribed treatment instructions provide a basis, along with other information (such as but not limited to information regarding the physical application setting), for determining corresponding radiation treatment plan optimization objectives.

At block 201, this process 200 provides a user interface such as the user interface 103 described above.

Figure 3:
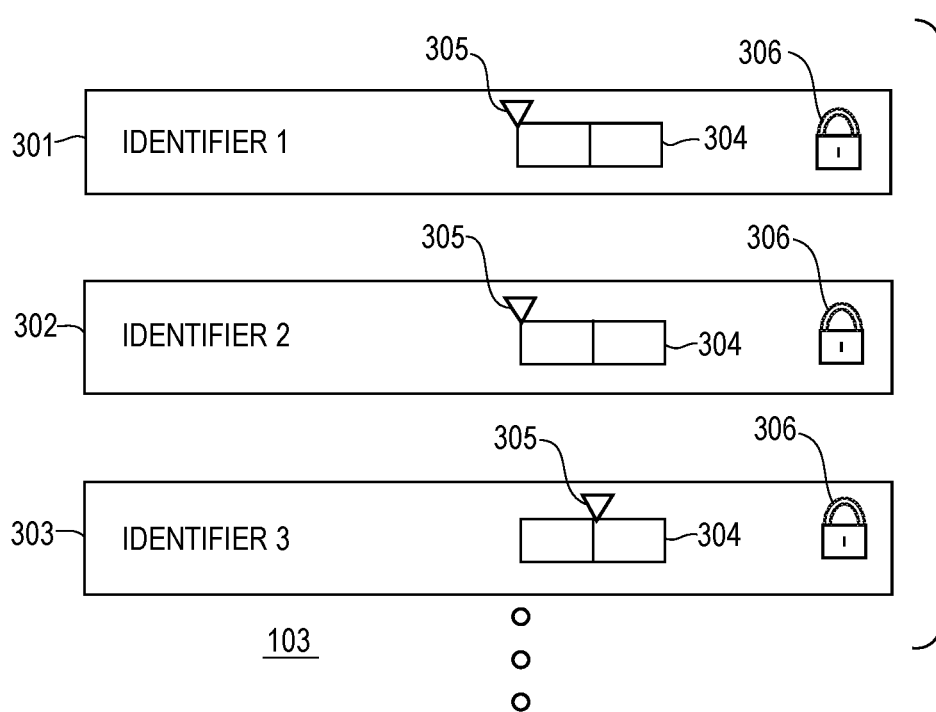
FIG. 3 comprises a partial screenshot as configured in accordance with various embodiments of these teachings.

At block 202 the control circuit 101 presents, on the user interface 103, a plurality of radiation-treatment clinical goals having an initial-state relative priority amongst themselves as established by a prescribing user. In particular, the prescribing user can both select the goals themselves as well as their relative priority. FIG. 3 provides an illustrative example in these regards. In this example, the user interface 103 presents at least three clinical goals (denoted by reference numerals 301-303).

In this example each of these clinical goals identifies a particular part of the patient's body by a corresponding identifier (represented in FIG. 3 by the generic identifiers "Identifier 1," "Identifier 2," and "Identifier 3"). The specific identifiers utilized in a given application setting can be as desired. Illustrative examples for such identifiers include, but are not limited to, "Brain," "Brainstem," "Middle Ear left," "Middle Ear right," "Eye right," "Eye left," "Optic Nerve left," "Optic Nerve right," "Chiasm," "Spinal Cord," and so forth.

In this example, the radiation-treatment clinical goals are presented in an order of presentation (i.e., one atop another). This order of presentation corresponds to, and sets, the relative priority of each of the radiation-treatment clinical goals vis-à-vis one another. In particular, in this example, a higher relative position of any given clinical goal indicates a relatively higher priority vis-à-vis clinical goals that are positioned relatively lower.

In this example, the presentation of each radiation-treatment clinical goal includes a graphic metric 304. This graphic metric 304 generally represents how well a particular dosing goal for the corresponding identified part is likely to be achieved. By one approach, the leftmost side of the graphic metric 304 can be colored green while the right most side of the graphic metric 304 can be colored red. If desired, a central portion can be colored differently, such as with the color yellow.

In each case, a triangle 305 serves to indicate the particular metric that corresponds to the particular identifier. In this simple illustrative example, this triangle 305 is located at the leftmost side of the graphic metric 304 for the first and second goals 301 and 302. This position indicates that the corresponding goal is very likely to be met. For the third goal 303, however, the triangle 305 is more centrally located and hence indicates that there is room for improvement. If the triangle 305 were to be further yet to the right, this would indicate that the clinical goal corresponding to that particular graphic metric 304 is unlikely to be met.

In this example, each of the clinical goals also includes a protection icon 306. In this example the protection icon 306 represents either of two possible states and also represents an opportunity for the user to switch between those two possible states. In a first state, and as illustrated in FIG. 3, the corresponding clinical goal is protected from having its corresponding achieved fluence-based radiation dose distribution reduced below some predetermined level notwithstanding subsequent user changes (as described below) to relative priorities amongst these radiation-treatment clinical goals. (In some cases the user may be provided with other tools that facilitate modifying the fluence/dose (such as painting the dose or modifying dose volume histogram lines). If desired, the aforementioned protection mechanism can also serve to similarly protect against all user actions and not only relative priority changes.)

By clicking on a particular one of these icons 306, the state changes to a second state. In this second state, the corresponding clinical goal is no longer protected as described above and hence the achieved fluence-based radiation dose distribution is no longer protected from potentially significant change if the user changes the aforementioned relative priorities (including other user-based changes if desired as described above).

Referring again to FIG. 2, at block 203 the control circuit 101 obtains (for example, from the aforementioned memory 102) a first set of rules. This first set of rules defines a fluence-based radiation dose distribution as a function of the plurality of radiation-treatment clinical goals and the relative priority amongst the plurality of radiation-treatment clinical goals. Fluence will be understood to represent radiative flux integrated over time and comprises a fundamental metric in dosimetry (i.e., the measurement and calculation of an absorbed dose of ionizing radiation in matter and tissue). The specific relationships that constitute this function can vary as desired with the requirements of a particular application setting. That said, for present purposes the fluence/dose need not literally represent the output of a standard, implementable treatment plan. Instead, to facilitate the simple comparative results provided herein, the fluence/dose need only mimic the trade-offs to some reasonable degree of correctness and need not be a real fluence or dose produced by a real treatment plan.

At block 204, the control circuit 101 obtains a second set of rules (again, if desired, from the aforementioned memory 102). This second set of rules specifies automatically saving, as corresponding states, information regarding relative priorities amongst the aforementioned plurality of radiation treatment clinical goals along with corresponding fluence-based radiation dose distributions as a function of detecting changes to the relative priorities amongst the plurality of radiation-treatment clinical goals.

At block 205 the control circuit 101 generates a first fluence-based radiation dose distribution for the particular patient by evaluating the plurality of radiation-treatment clinical goals and the relative priority amongst the plurality of radiation-treat medical goals against the aforementioned first set of rules. At block 206 the control circuit 101 then presents information regarding the first fluence-based radiation dose distribution for the particular patient via, for example, the aforementioned user interface 103. That information can be conveyed, for example, via the aforementioned graphic metric 304 for each of the clinical goals.

At block 207 the control circuit 101 automatically saves, as a corresponding first state, information regarding the relative priority amongst the plurality of radiation-treatment clinical goals and the corresponding first fluence-based radiation dose distribution for the particular patient. By one approach, the saved first-state information includes fluence information but not corresponding calculated dose distribution results as such. So configured, the prescribing user (such as a doctor) can readily view and get a general sense of how well each of the clinical goals are likely to be met when a corresponding radiation treatment plan is formulated and optimized.

Referring now to FIG. 4, description of this process 200 will continue.

At optional block 401, the control circuit 101 provides an opportunity, via the user interface 103, for the prescribing user to selectively change the relative priority amongst the plurality of radiation-treatment clinical goals. As noted above with respect to the description of FIG. 3, in this example the relative priority of each radiation-treatment clinical goal is represented as a function of the relative position of these goals with respect to one another. Accordingly, in this illustrative example, the aforementioned opportunity to selectively change that relative priority comprises an opportunity to select and move (for example, by a click-and-drag capability) the relative position of at least one of the radiation-treatment clinical goals.

Figure 5:
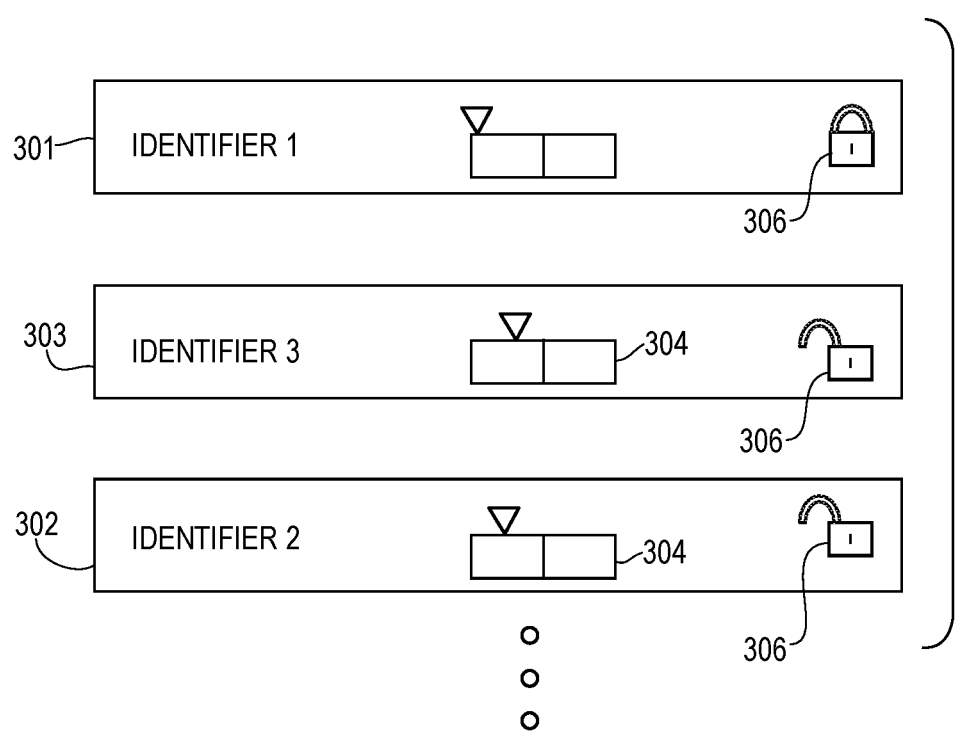
FIG. 5 comprises a partial screenshot as configured in accordance with various embodiments of these teachings.

FIG. 5 provides a simple illustrative example in these regards. In this example, the prescribing user selected the second clinical goal 302 pertaining to Identifier 2 and dragged that goal 302 to below the third clinical goal 303. In this example the control circuit 101 automatically rearranges the clinical goals as necessary to remove gaps.

Following the rearrangement of the clinical goals as described, the first clinical goal 301 has a highest priority, followed by the third clinical goal 303 which has a second highest priority and the second clinical goal 302 which now has a third highest priority.

In the illustrative example of FIG. 5, it can also be seen that the prescribing user clicked on the protection icons 306 for the second and third clinical goals 302 and 303. Accordingly, the previously-obtained results are no longer protected in the manner described above. The first clinical goal 301, however, remains protected as described above.

At block 402 of FIG. 4, the control circuit detects the above-described rearrangement of the clinical goals and identifies the corresponding change to the relative priority amongst the clinical goals. At block 403, and in response to the prescribing user changing the relative priority amongst the plurality of radiation-treatment clinical goals, the control circuit 101 generates a second fluence-based radiation dose distribution for the particular patient by evaluating the plurality of radiation-treatment clinical goals and the changed relative priority amongst the plurality of radiation-treatment clinical goals against the aforementioned first set of rules.

At block 404 the control circuit 101 presents information regarding the second fluence-based radiation dose distribution for the particular patient. As illustrated in FIG. 5, the graphic metric 304 for the second clinical goal 302 is less favorable for this second state than for the first state illustrated in FIG. 3 but is nevertheless still favorable. At the same time, the graphics metric 304 for the third clinical goal 303 has now shifted from an unfavorable (or nearly unfavorable) state to a more favorable state. On balance, the prescribing user can easily discern the general impact that changing the original prioritization of the clinical goals has upon an ability to actually achieve the desired goals.

At block 405, the control circuit uses the second set of rules to automatically save, as a corresponding second state, information regarding the changed relative priority amongst the plurality of radiation-treatment clinical goals and the corresponding second fluence-based radiation dose distribution for the particular patient. That information can be saved, for example, in the above-mentioned memory 102.

If desired, the activities described above in blocks 401 through 405 can be repeated as many times as desired to thereby derive and store additional states representing other prioritizations of the clinical goals.

At block 406, the control circuit 101 provides an opportunity, via the user interface 103, for the prescribing user to switch back and forth between a display of information corresponding to the above-described first state and second state. Such a capability can greatly simplify presenting that information in a way that easily and intuitively illustrates dosing trade-offs that correspond to prioritization amongst the radiation-treatment clinical goals. Such an opportunity can comprise, for example, a user-assertable button displayed on the user interface 103.

At block 407, this process permits the control circuit 101 to provide an opportunity, again via the user interface 103, for the prescribing user to cancel all user changes to the relative priority amongst the clinical goals. Such an opportunity can also comprise a user-assertable button displayed on the user interface 103. In response to selecting this opportunity the control circuit 101 can automatically present the plurality of radiation-treatment clinical goals using the initial-state relative priority amongst those goals along with the information regarding the first fluence-based radiation dose distribution for the particular patient.

These teachings provide a simple yet powerful way to help a prescribing user visualize how changes to the relative prioritization amongst a plurality of radiation-treatment clinical goals result in corresponding dosing trade-offs that are represented as fluence-based radiation dose distributions. Successfully employing these teachings requires virtually no training for the prescribing users and, in particular, does not require any in-depth training regarding the technical nuances involved with setting optimization objectives. At the same time, by allowing prescribing users to test and modify the relative prioritizations of their clinical goals, the dosing prescription provided by the prescribing user for use by optimization technicians, dosimetrists, medical physicists, and clinicians is more likely to provide useful input upon which optimization objectives for a radiation treatment plan can be based.

Those skilled in the art will recognize that a wide variety of modifications, alterations, and combinations can be made with respect to the above described embodiments without departing from the scope of the invention. As one example in that regard, the control circuit can be configured to use the user interface to allow the prescribing user to save any state at will and to later selectively return to that saved state as they wish. Accordingly such modifications, alterations, and combinations are to be viewed as being within the ambit of the inventive concept.

What is claimed is:

1. A method for formulating patient treatment prescription instructions for radiation therapy, which patient treatment prescription instructions are configured for use to determine corresponding radiation treatment plan optimization objectives for creation of an optimized radiation treatment plan for a particular patient using a particular radiation treatment platform, wherein the patient treatment prescription instructions do not accommodate technical details and specifications of the particular radiation treatment platform, the method comprising:

providing a user interface;

presenting on the user interface a plurality of radiation-treatment prescription instructions that prescribe a particular radiation dosage for particular parts of the particular patient, wherein each of the radiation-treatment prescription instructions has an initial-state relative priority as compared to others of the plurality of radiation-treatment prescription instructions;

determining a pre-optimization first fluence-based radiation dose distribution for the particular patient as a function of the plurality of radiation-treatment prescription instructions and the initial-state relative priority for each of the plurality of radiation-treatment prescription instructions and presenting pre-optimization information regarding the pre-optimization first fluence-based radiation dose distribution for the particular patient;

automatically saving, as a corresponding first state, pre-optimization information regarding relative priorities amongst the plurality of radiation-treatment prescription instructions and the corresponding pre-optimization first fluence-based radiation dose distribution for the particular patient;

in response to a user changing, via the user interface, a relative priority for at least one of the plurality of radiation-treatment prescription instructions to thereby provide a changed relative priority amongst the plurality of radiation-treatment prescription instructions, dynamically determining a pre-optimization second fluence-based radiation dose distribution for the particular patient as a function of the plurality of radiation-treatment prescription instructions and the changed relative priority amongst the plurality of radiation-treatment prescription instructions and presenting pre-optimization information regarding the pre-optimization second fluence-based radiation dose distribution for the particular patient;

automatically saving, as a corresponding second state, pre-optimization information regarding the changed relative priority amongst the plurality of radiation-treatment prescription instructions and the corresponding pre-optimization second fluence-based radiation dose distribution for the particular patient;

displaying, on the user interface, visual information regarding changes to fluence-based dose distribution information that occur in response to changes to relative prioritization amongst the plurality of radiation-treatment prescription instructions to thereby illustrate, prior to optimizing a corresponding radiation treatment plan, dosing tradeoffs that correspond to prioritization amongst the radiation-treatment prescription instructions.

2. The method of claim 1 wherein presenting on the user interface the plurality of radiation-treatment prescription instructions comprises presenting the radiation-treatment prescription instructions in an order of presentation, wherein a relative position of a particular one of the radiation-treatment prescription instructions establishes the relative priority for that particular one of the radiation-treatment prescription instructions.

3. The method of claim 2 further comprising:
detecting the user selectively changing, via the user interface, a relative priority for at least one of the plurality of radiation-treatment prescription instructions.

4. The method of claim 3 wherein the detecting the user selectively changing a relative priority for at least one of the plurality of radiation-treatment prescription instructions comprises detecting the user selecting and moving, on the user interface, a relative position of at least one of the radiation-treatment prescription instructions.

5. The method of claim 4 wherein the selecting and moving comprises clicking-and-dragging one of the plurality of radiation-treatment prescription instructions.

6. The method of claim 1 further comprising:
switching back and forth between a display of information corresponding to the first state and the second state on the user interface.

7. The method of claim 1 further comprising:
canceling, via the user interface, all changes to the relative priority for any of the radiation-treatment prescription instructions and, in response thereto, presenting the plurality of radiation-treatment prescription instructions using the initial-state relative priority along with the information regarding the first fluence-based radiation dose distribution for the particular patient.

8. The method of claim 1 wherein automatically saving, as a corresponding state, pre-optimization information regarding the corresponding fluence-based radiation dose distribution for the particular patient comprises storing fluence information but not corresponding calculated dose distribution results.

9. The method of claim 1 wherein at least one of the plurality of radiation-treatment prescription instructions clinical goals constitutes a goal for a treatment volume and at least one of the plurality of radiation-treatment prescription instructions constitutes a goal for an organ-at-risk.

10. The method of claim 1 further comprising:
protecting, via the user interface, an achieved fluence-based radiation dose distribution that corresponds to one of the plurality of radiation-treatment prescription instructions notwithstanding subsequent changes to the relative priority for at least one of the plurality of radiation-treatment prescription instructions.

11. A method for formulating patient treatment prescription instructions for radiation therapy, which patient treatment prescription instructions are configured for use to determine corresponding radiation treatment plan optimization objectives for creation of an optimized radiation treatment plan for a particular patient using a particular radiation treatment platform, using automatically-iterated radiation treatment plan optimization, wherein the patient treatment prescription instructions do not accommodate technical details and specifications of the particular radiation treatment platform, the method comprising:

providing a user interface;

presenting on the user interface a plurality of radiation-treatment prescription instructions that prescribe a particular radiation dosage for particular parts of the particular patient, wherein each of the radiation-treatment prescription instructions has an initial-state relative priority as compared to others of the plurality of radiation-treatment prescription instructions;

obtaining a first set of rules that define a pre-optimization fluence-based radiation dose distribution as a function of the plurality of radiation-treatment prescription instructions and the relative priority for each of the plurality of radiation-treatment prescription instructions;

obtaining a second set of rules that specify automatically saving, as corresponding states, pre-optimization information regarding relative priorities amongst the plurality of radiation-treatment prescription instructions and corresponding fluence-based radiation dose distributions as a function of detecting changes to the relative priority of any of the plurality of radiation-treatment prescription instructions;

generating a pre-optimization first fluence-based radiation dose distribution for the particular patient by evaluating the plurality of radiation-treatment prescription instructions and the relative priority for each of the plurality of radiation-treatment prescription instructions against the first set of rules;

presenting pre-optimization information regarding the pre-optimization first fluence-based radiation dose distribution for the particular patient;

automatically saving, as a corresponding first state, pre-optimization information regarding the relative priority the plurality of radiation-treatment prescription instructions and the corresponding pre-optimization first fluence-based radiation dose distribution for the particular patient;

in response to a user changing, via the user interface, a relative priority for at least one of the plurality of radiation-treatment prescription instructions to thereby provide a changed relative priority amongst the plurality of radiation-treatment prescription instructions, generating a pre-optimization second fluence-based radiation dose distribution for the particular patient by evaluating the plurality of radiation-treatment prescription instructions and the changed relative priority amongst the plurality of radiation-treatment prescription instructions against the first set of rules;

presenting pre-optimization information regarding the pre-optimization second fluence-based radiation dose distribution for the particular patient;

using the second set of rules to automatically save, as a corresponding second state, pre-optimization information regarding the changed relative priority amongst the plurality of radiation-treatment prescription instructions and the corresponding pre-optimization second fluence-based radiation dose distribution for the particular patient;

displaying visual information regarding changes to fluence-based dose distribution information that occur in response to changes to relative prioritization amongst the plurality of radiation-treatment prescription instructions to thereby illustrate, prior to optimizing a corresponding radiation treatment plan, dosing tradeoffs that correspond to prioritization amongst the radiation-treatment prescription instructions.

12. The method of claim 11 wherein presenting on the user interface the plurality of radiation-treatment prescription instructions comprises presenting the radiation-treatment prescription instructions in an order of presentation, wherein a relative position of a particular one of the radiation-treatment prescription instructions establishes the relative priority for that particular one of the radiation-treatment prescription instructions.

13. The method of claim 12 further comprising:
detecting the user selectively changing a relative priority for at least one of the plurality of radiation-treatment prescription instructions.

14. The method of claim 13 wherein the detecting the user selectively changing a relative priority for at least one of the plurality of radiation-treatment prescription instructions comprises detecting the user selecting and moving, on the user interface, a relative position of at least one of the radiation-treatment prescription instructions.

15. The method of claim 14 wherein the selecting and moving comprises clicking-and-dragging a particular one of the radiation-treatment prescription instructions.

16. The method of claim 11 further comprising:
switching back and forth between a display of information corresponding to the first state and a display of the second state.

17. The method of claim 11 further comprising:
cancelling all changes to the relative priority for any of the radiation-treatment prescription instructions and, in response thereto, presenting the plurality of radiation-treatment prescription instructions using the initial-state relative priority along with the information regarding the pre-optimization first fluence-based radiation dose distribution for the particular patient.

18. The method of claim 11 wherein automatically saving, as a corresponding state, pre-optimization information regarding the corresponding fluence-based radiation dose distribution for the particular patient comprises storing fluence information but not corresponding calculated dose distribution results.

19. The method of claim 11 wherein at least one of the plurality of radiation-treatment prescription instructions constitutes a goal for a treatment volume and at least one of the plurality of radiation-treatment prescription instructions constitutes a goal for an organ-at-risk.

* * * * *